(12) United States Patent
Murray

(10) Patent No.: US 7,862,532 B2
(45) Date of Patent: Jan. 4, 2011

(54) PUNCTUM PLUGS HAVING INSERTION GUIDES AND STRENGTHENING BEAMS

(75) Inventor: George W. Murray, Memphis, TN (US)

(73) Assignee: Delta Life Sciences, Inc., Memphis, TN (US)

( * ) Notice: Subject to any disclaimer, the term of this patent is extended or adjusted under 35 U.S.C. 154(b) by 391 days.

(21) Appl. No.: 11/246,894

(22) Filed: Oct. 7, 2005

(65) Prior Publication Data

US 2007/0083146 A1 Apr. 12, 2007

(51) Int. Cl.
*A61M 5/00* (2006.01)
*A61B 17/00* (2006.01)

(52) U.S. Cl. .......................................... 604/9; 128/887

(58) Field of Classification Search ............... 604/7–10, 604/500, 521, 19, 27, 28, 264, 294, 107, 604/108, 289, 290, 540, 541, 523, 317, 285, 604/907; 606/185, 167, 191, 107, 108; 623/4.1, 623/11.11, 23.71, 23.64

See application file for complete search history.

(56) References Cited

U.S. PATENT DOCUMENTS

| | | | |
|---|---|---|---|
| 3,949,750 A | 4/1976 | Freeman | |
| 4,915,684 A | 4/1990 | MacKeen et al. | |
| 4,959,048 A | 9/1990 | Seder et al. | |
| 5,171,270 A | 12/1992 | Herrick | |
| 5,283,063 A | 2/1994 | Freeman | |
| 5,334,137 A | 8/1994 | Freeman | |
| 5,417,651 A | 5/1995 | Guena et al. | |
| 5,423,777 A | 6/1995 | Tajiri et al. | |
| 5,723,005 A | 3/1998 | Herrick | |
| 5,741,292 A | 4/1998 | Mendius | |
| 5,807,302 A | 9/1998 | Wandel | |
| 5,807,303 A | 9/1998 | Bays | |
| 5,830,171 A | 11/1998 | Wallace | |
| 6,016,806 A | 1/2000 | Webb | |
| 6,027,470 A | 2/2000 | Mendius | |
| 6,041,785 A | 3/2000 | Webb | |
| 6,082,362 A | 7/2000 | Webb | |
| 6,149,684 A | 11/2000 | Herrick | |
| 6,196,993 B1 | 3/2001 | Cohan et al. | |
| 6,234,175 B1 | 5/2001 | Zhou et al. | |
| 6,290,684 B1 | 9/2001 | Herrick | |
| 6,306,114 B1 | 10/2001 | Freeman et al. | |
| 6,344,047 B1 | 2/2002 | Price et al. | |
| 6,527,780 B1 | 3/2003 | Wallace et al. | |
| 2004/0231679 A1 | 11/2004 | Prescott et al. | |
| 2004/0254516 A1 | 12/2004 | Murray et al. | |
| 2005/0197614 A1 | 9/2005 | Pritchard et al. | |

FOREIGN PATENT DOCUMENTS

GB 2 069 339 A 8/1981

*Primary Examiner*—Leslie R Deak

(57) ABSTRACT

A punctum plug comprises a distal tip for anchoring the punctum plug in an implanted position in the lacrimal drainage system of the eye, a proximal cap that remains exposed in the eye in the implanted position, and a body connecting the distal tip to the cap. The distal tip includes a plurality of longitudinal depressions along its outer surface to facilitate implantation, and one or more strengthening beams to resist deformation or collapse of the punctum plug.

26 Claims, 7 Drawing Sheets

PUNCTUM PLUGS HAVING INSERTION GUIDES AND STRENGTHENING BEAMS

BACKGROUND OF THE INVENTION

1. Field of the Invention

The present invention relates generally to the treatment of tear fluid or moisture deficiencies in the eye and, more particularly, to punctum plugs and methods of punctal occlusion for deterring the drainage of tear fluid or moisture from the eye.

2. Brief Discussion of the Related Art

Normally the eye is protected and lubricated by a film of naturally produced tear fluid spread over the corneal and conjunctival epithelia through blinking. Various problems may arise in the eye, however, where the quantity of tear fluid or moisture in the eye is deficient, and the problem of insufficient tear fluid or moisture in the eye may be referred to generally as dry eye syndrome or disorder. Tear fluid or moisture deficiencies are oftentimes chronic and may result from inadequate tear fluid production and/or drainage of too much tear fluid or moisture from the eye through the lacrimal drainage system of the eye. Various conditions may cause and/or aggravate tear fluid or moisture deficiencies including disease such as cataracts, inflammation, congenital defects, side effects of over-the-counter and prescription drugs, allergies, environmental irritants or effects, atrophy, aging, eye strain, contact lens use, and procedures performed on the eye such as LASIK and cataract procedures.

Dry eye syndrome is increasing in prevalence and it is estimated that up to 40% of the U.S. population suffers from dry eye syndrome to some extent. Dry eye syndrome may manifest as various ophthalmic ailments including general irritation and/or discomfort, itchy, gritty, sticky and/or burning sensations, conjunctivitis, blepharitis, contact lens problems, corneal erosion, incipient corneal graft rejection, recurrent chalzion, pinguecula, corneal ulcers and acute lid abscesses. Sinus ailments, hay fevers, colds and other recurrent infections have been attributed to dry eye syndrome.

One common treatment for dry eye syndrome involves the introduction of artificial tear fluid into the eye. The benefits derived from artificial tear fluids are limited and are usually of short duration. In some users, artificial tear fluids have caused toxic reactions. Other drawbacks of artificial tear fluids include possible blurred vision and unsightly deposits on the eyelids.

Mechanical devices such as punctum plugs which block or occlude the punctum to deter drainage of tear fluid from the eye have been proposed and are represented by U.S. Pat. Nos. 3,949,750 and 5,283,063 to Freeman, U.S. Pat. No. 4,915,684 to MacKeen et al, U.S. Pat. No. 4,959,048 to Seder et al, U.S. Pat. Nos. 5,723,005, 6,149,684 and 6,290,684 B1 to Herrick, U.S. Pat. No. 5,417,651 to Guena et al, U.S. Pat. No. 5,423,777 to Tajiri et al, U.S. Pat. Nos. 5,741,292 and 6,027,470 to Mendius, U.S. Pat. No.5,830,171 to Wallace, U.S. Pat. Nos. 6,016,806 and 6,041,785 to Webb, U.S. Pat. No. 6,234,175 B1 to Zhou et al, U.S. Pat. No. 6,306,114 B1 to Freeman et al, U.S. Pat. No. 6,344,047 B1 to Price et al, U.S. Patent Application Publication No. US 2004/0254516 A1, and U.S. Patent Application Publication No. US 2005/0197614 A1.

Typically, punctum plugs are implanted in the eye using insertion tools, and punctum plugs having axial passages for releasably engaging the insertion tools have been proposed as represented by U.S. Pat. No. 3,949,750 to Freeman, U.S. Pat. No. 4,915,684 to MacKeen et al, U.S. Pat. No. 5,171,270 to Herrick, U.S. Pat. Nos. 5,283,063 and 5,334,137 to Freeman, U.S. Pat. No. 5,423,777 to Tajiri et al, U.S. Pat. No. 5,723,005 to Herrick, U.S. Pat. Nos. 5,741,292 and 6,027,470 to Mendius, U.S. Pat. No. 5,830,171 to Wallace, U.S. Pat. No. 6,016,806 to Webb, U.S. Pat. No. 6,149,684 to Herrick, U.S. Pat. No. 6,306,114 B1 to Freeman et al, U.S. Pat. No. 6,344,047 B1 to Price et al, U.S. Pat. No. 6,527,780 B1 to Wallace et al, U.S. Patent Application Publication No. US 2004/0254516 A1, and U.S. Patent Application Publication No. US 2005/0197614 A1.

Punctum plugs typically include a proximal head, a distal tip and a shaft connecting the proximal head and the distal tip. The shaft is usually smaller in cross-sectional size than the proximal head and the distal tip. A punctum plug is usually inserted, distal tip first, in a punctal opening of the punctum and is advanced distally in the punctum until the proximal head is seated on the punctal opening. The proximal head is normally larger than the punctal opening such that the proximal head does not pass through the punctal opening and remains exposed in the eye. The distal tip typically has a cross-sectional size to fill the canalicular canal which is in communication with the punctal opening and to anchor the punctum plug in place. Usually the proximal head overlaps and is in abutment with a rim of anatomical tissue circumscribing the punctal opening to better block the punctal opening and prevent displacement or migration of the punctum plug into the punctum. The blockage or occlusion presented by the punctum plug deters tear fluid from draining from the eye through the punctal opening and the corresponding canalicular canal from which tear fluid would otherwise drain into the lacrimal sac and through the nasolacrimal duct into the nasal cavity. The proximal head of the punctum plug remaining exposed in the eye may be engaged with the insertion tool or other instrument by which the punctum plug may be withdrawn through the punctal opening for removal from the eye.

Intracanalicular implants have been proposed which are disposed entirely within the canalicular canal without exposure or protrusion thereof in the eye, and such implants are illustrated by U.S. Pat. Nos. 4,660,546, 5,049,142 and 5,053,030 to Herrick et al, and U.S. Pat. No. 5,163,959 and 5,171,270 to Herrick. Intracanalicular implants which are disposed entirely within the canalicular canal are more difficult to implant and remove, and are more likely to be implanted improperly or to become displaced in the canalicular canal. Accordingly, punctum plugs present advantages over intracanalicular implants as a treatment for dry eye syndrome or disorder.

A problem of many punctum plugs is that they may undesirably or excessively deform or collapse, especially during implantation, due to insufficient structural strength or rigidity. Where a punctum plug undesirably or excessively deforms, collapses or undergoes a "noodling" action during implantation, it is more difficult and time consuming to implant the punctum plug correctly. A punctum plug that undesirably or excessively deforms, collapses or undergoes a "noodling" action during implantation may end up being improperly implanted including implanted too far or not far enough into the punctum, implanted off-center or skewed in the punctum and/or implanted without the distal tip being securely anchored in the canalicular canal. Once implanted, a punctum plug that later excessively or undesirably deforms or collapses due to insufficient strength or rigidity could migrate from its implanted position. An incorrectly implanted punctum plug or one that has migrated after implantation may be less effective at deterring fluid drainage, could cause trauma or discomfort to the patient, and may be more difficult to remove from the eye. It would be desirable, therefore, to increase the strength and rigidity of punctum plugs to resist undesirable or excessive deformation or collapse, especially during implantation.

Another problem of punctum plugs is that the punctum plugs do not well adapt to various different anatomical characteristics found in the puncta of different patients. Depending on the individual anatomy of a patient, the punctal opening may be exposed on the surface of the eyelid or may be introverted on the lid margin and lying against the surface of the conjunctiva of the eye. The punctal opening has a funnel shape which can be essentially circular or, more commonly, non-circular or slit-like. A punctal opening that is non-circular generally has a longer (major) axis or dimension extending lengthwise and a shorter (minor) axis or dimension extending widthwise, with the length and width dimensions varying on an individual patient basis. During insertion of conventional punctum plugs through non-circular punctal openings, undesirable or excessive stress or force may be exerted on the anatomical tissue of the punctum as the narrower width dimension of the punctal opening is widened in order to accommodate the punctum plug. Consequently, implantation of the punctum plug is made more difficult and places the patient at risk of trauma. It would be beneficial for an individual punctum plug to better adapt to a wide range of different anatomical puncta to ease insertion of the punctum plug in puncta having both circular and non-circular punctal openings.

Punctum plugs may be made available in different sizes corresponding to anatomical puncta and canaliculi of different cross-sectional sizes. It is important for maximum effectiveness and proper fit that the correct size punctum plug be selected for implantation in the punctum of a patient. Due to the microscopic size of punctum plugs, however, identifying and selecting a punctum plug of the correct size for a patient is generally time consuming and tedious due to the difficulty involved in distinguishing between different size punctum plugs. It would therefore be advantageous to enable punctum plugs to be visually identified or differentiated by size with greater certainty and in as little time as possible.

SUMMARY OF THE INVENTION

The present invention is generally characterized in a punctum plug including a distal tip, a proximal cap, and a body connecting the distal tip to the cap. The distal tip has a forward end surface, a rearward end surface, and a main section extending longitudinally between the forward and rearward end surfaces. The distal tip has a configuration to anchor or secure the punctum plug in an implanted position in the lacrimal drainage system of the eye. The proximal cap has a configuration to remain exposed in the eye in the implanted position. The distal tip includes a plurality of longitudinal depressions along an outer surface of the main section to facilitate implantation of the punctum plug. The depressions are located on the distal tip at spaced radial locations about a central longitudinal axis of the punctum plug. Preferably, the distal tip has two depressions disposed at respective radial locations spaced 180° from one another about the central longitudinal axis of the punctum plug. Each depression has a curved floor recessed from the outer surface of the main section, and side walls extending from the outer surface to the floor. The floor is preferably continuously curving with a concave curvature, and the side walls are preferably planar and parallel to one another. The distal tip is provided with one or more beams or protrusions on the rearward end surface to strengthen or rigidify the punctum plug to resist deformation or collapse, especially during implantation. Each protrusion preferably has a convex configuration including partial spherical and hemispherical configurations. Different size punctum plugs can be provided with different numbers of protrusions such that the number of protrusions identifies the size of the punctum plug.

Various objects, advantages and benefits of the invention will become apparent from the following description of the preferred embodiments taken in conjunction with the accompanying drawings wherein like parts in each of the several figures are identified by the same or similar reference characters.

DESCRIPTION OF THE PREFERRED EMBODIMENTS

Figure 1:
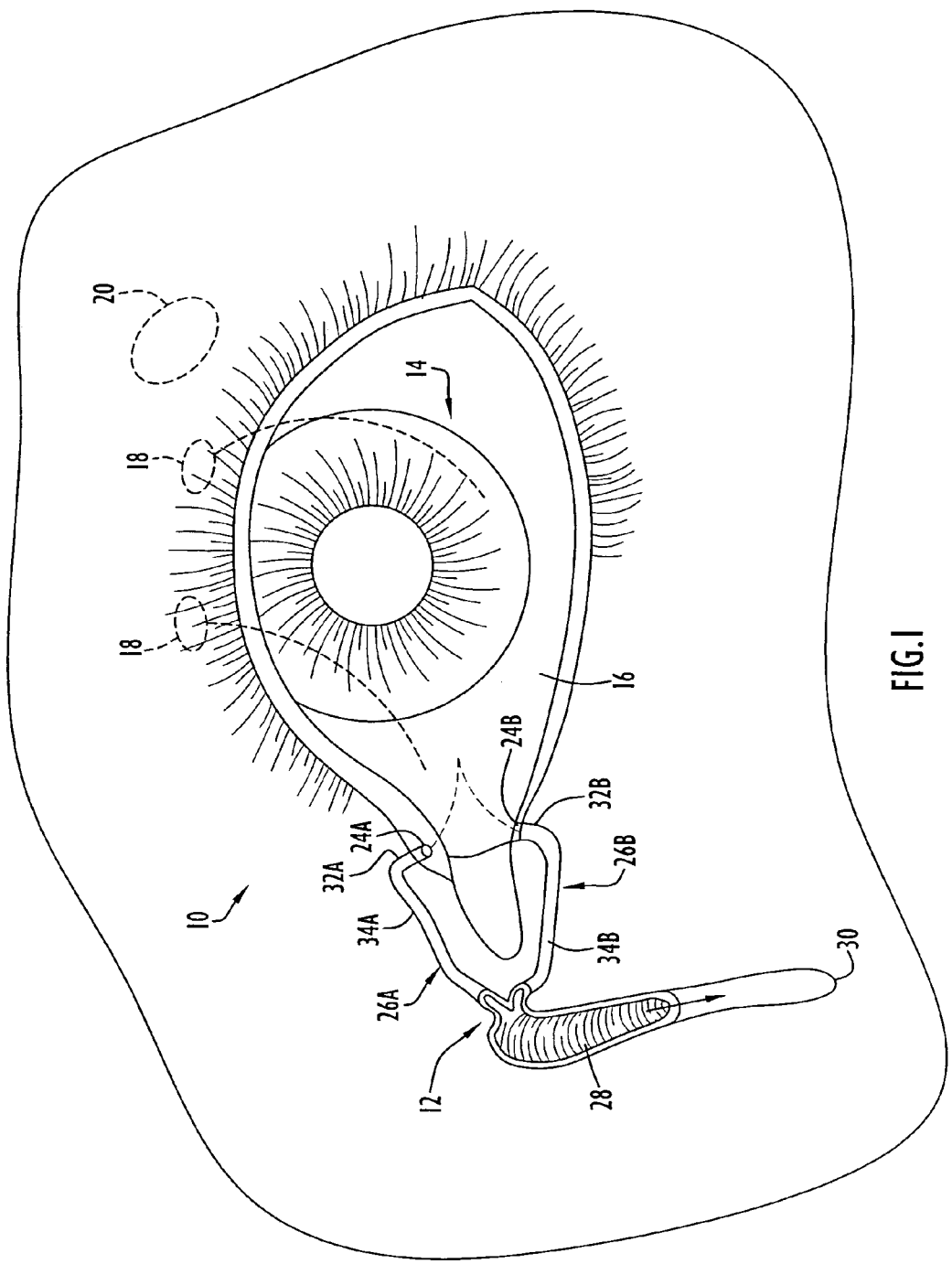
FIG. 1 is an anatomical representation of the lacrimal drainage system of the eye.

FIG. 1 depicts an eye 10 and its lacrimal drainage system 12. The eye 10 comprises an eyeball 14 having a cornea 16. A series of small lacrimal glands 18 spaced apart from one another above the cornea 16 produce constant tears, and a large lacrimal gland 20 produces crying tears. The cornea 16 and the inner surfaces of the eyelids are moisturized and lubricated by tear fluid, which forms a tear film over the cornea 16. The tear film serves to wet and lubricate the eye through a balance of an outer lipid (oily) layer, a middle aqueous (watery) layer and an inner mucin (mucous) layer. Tear fluid drains from the eye through the lacrimal drainage system 12 comprising upper punctum and lower punctum having upper and lower punctal openings 24a and 24b, respectively, communicating with respective upper and lower canalicular canals 26a and 26b leading to lacrimal sac 28 having a nasolacrimal duct 30. The upper and lower punctal openings 24a and 24b are generally located at the inner corner of the upper and lower eyelids, respectively, and are each circumscribed by a rim of anatomical tissue. Depending on individual anatomy, the punctal openings may be exposed on the surface of the eyelid or may be introverted on the eyelid margin and lying against the surface of the conjunctiva of the eye. Each punctal opening 24a and 24b has a funnel shape which can be circular or, more commonly, non-circular or slit-like. Non-circular punctal openings have a longer or major axis or dimension extending along the length of the punctal opening and a shorter or minor axis or dimension extending along the width of the punctal opening, with the length and width dimensions varying on an individual basis. In the most commonly observed situations, therefore, the punctal openings are larger in size along one dimension, i.e. length, and are smaller in size along another dimension, i.e. width. The upper and lower canalicular canals 26a and 26b comprise respective vertical canalicular portions 32a and 32b extending from the punctal openings 24a and 24b to respective horizontal canalicular canal portions 34a and 34b extending to the lacrimal sac 28.

Tear fluid normally drains from the eye through the punctal openings 24a and 24b, the upper and lower canalicular canals 26a and 26b, the lacrimal sac 28 and the nasolacrimal duct 30 into the nasal cavity. The majority of tear fluid drains through the lower punctum. Implantation of a punctum plug in the upper punctum and/or lower punctum to deter drainage of tear fluid or moisture from the eye through the lacrimal drainage system 12 is used as a treatment for dry eye syndrome or disorder arising from insufficient moisture or tear fluid in the eye.

Figure 2:
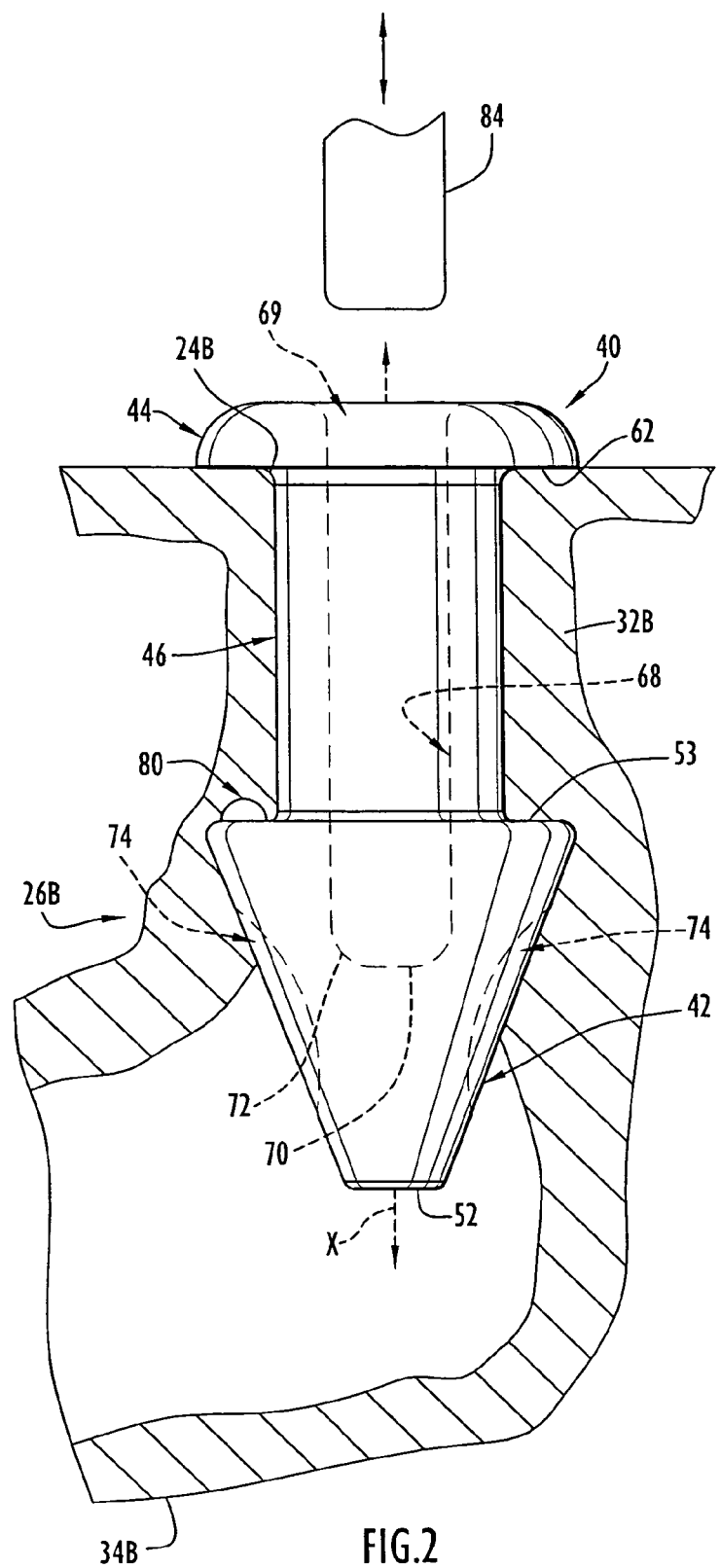
FIG. 2 is a broken side view, partly in section, of the lacrimal drainage system with a punctum plug of the present invention implanted therein.

A punctum plug 40 is shown in FIGS. 2-9, the punctum plug 40 being depicted in FIG. 2 implanted in the lacrimal drainage system 12 to deter or block the drainage of tear fluid or moisture from the eye 10 via the lacrimal drainage system. The punctum plug 40 comprises a distal tip 42 or anchor member, a proximal cap or head 44, and a body or shaft 46 connecting the tip 42 to the cap 44. The tip 42 comprises a main section 48 of frustoconical configuration between forward and rearward rims 50 and 51 respectively terminating at forward and rearward end surfaces 52 and 53. The forward and rearward end surfaces 52 and 53 are planar and are parallel to each other as well as being transverse or perpendicular to a central longitudinal axis X of the punctum plug 40. The forward and rearward end surfaces 52 and 53 have circular peripheral configurations. The forward rim 50 extends from the circumference of the forward end surface 52 to a forward circumferential edge 54 of the frustoconical main section 48. The rearward rim 51 extends from the circumference of the rearward end surface 53 to a rearward circumferential edge 55 of the main section 48. The forward and rearward circumferential edges 54 and 55 are disposed in respective planes parallel to the forward and rearward end surfaces 52 and 53.

Figure 5:
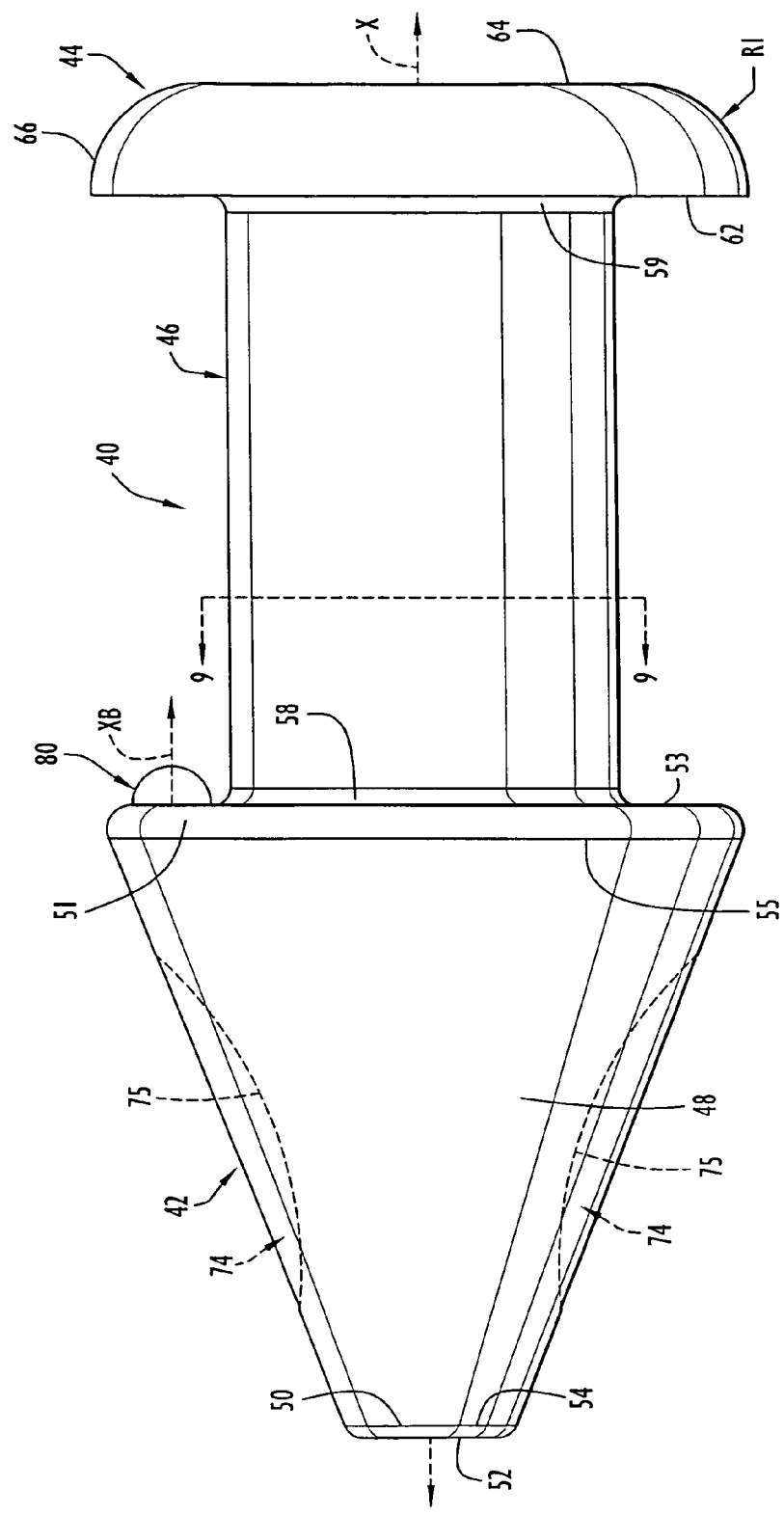
FIG. 5 is a longitudinal side view of the punctum plug.

The circumference of the forward end surface 52 is smaller than the circumference of the forward circumferential edge 54, and the forward rim 50 has an arcuate curvature in profile between the circumference of the forward end surface 52 and the forward circumferential edge 54 as seen in FIG. 5 to provide a smooth, gradual, gently rounded transition between the forward end surface 52 and the main section 48 at the forward end of the tip 42. The circumference of the rearward end surface 53 is smaller than the circumference of the rearward circumferential edge 55, and the rearward rim 51 has an arcuate curvature in profile between the circumference of the rearward end surface 53 and the rearward circumferential edge 55 to provide a smooth, gently rounded transition between the rearward end surface 53 and the main section 48 at the rearward end of tip 42. The rearward rim 51 has a radius of curvature imparting a convex configuration to the rearward rim 51 between the rearward end surface 53 and the rearward circumferential edge 55, and the rearward rim 51 defines a maximum external diameter for the distal tip 42. The distal tip 42 has a minimum external diameter along the forward rim 50. The main section 48 has a circular configuration in external cross-section continuously tapering from the rearward circumferential edge 55 to the forward circumferential edge 54. Accordingly, the distal tip 42 has a maximum or wider external dimension at or near its rearward end and a minimum or narrower external dimension at or near its forward end. The tip 42 has a length between the forward and rearward end surfaces 52 and 53.

The body 46 extends longitudinally between the tip 42 and the cap 44 and is essentially cylindrical in external configuration with a uniform and constant circular external cross-section between flared forward and rearward junctions 58 and 59 respectively joining opposite ends of the body 46 to the tip 42 and the cap 44. As best seen in FIG. 5, the forward junction 58 has a concave curvature from the outer circumferential surface of the body 46 to the rearward end surface 53 of tip 42. The rearward junction 59 has a concave curvature from the outer circumferential surface of the body 46 to a distal or forward end wall 62 of cap 44. The junctions 58 and 59 respectively provide a smooth, gentle and gradual transition between the outer circumferential surface of the body 46 and the rearward end surface 53 of tip 42 and the distal end wall 62 of cap 44. The outer or external diameter of the body 46 is less than the maximum external diameter of tip 42 and is less than the outer or external diameter of distal end wall 62 as explained further below. The body 46, including the forward and rearward junctions 58 and 59, has a length between the rearward end surface 53 of tip 42 and the distal end wall 62 of cap 44.

Figure 6:
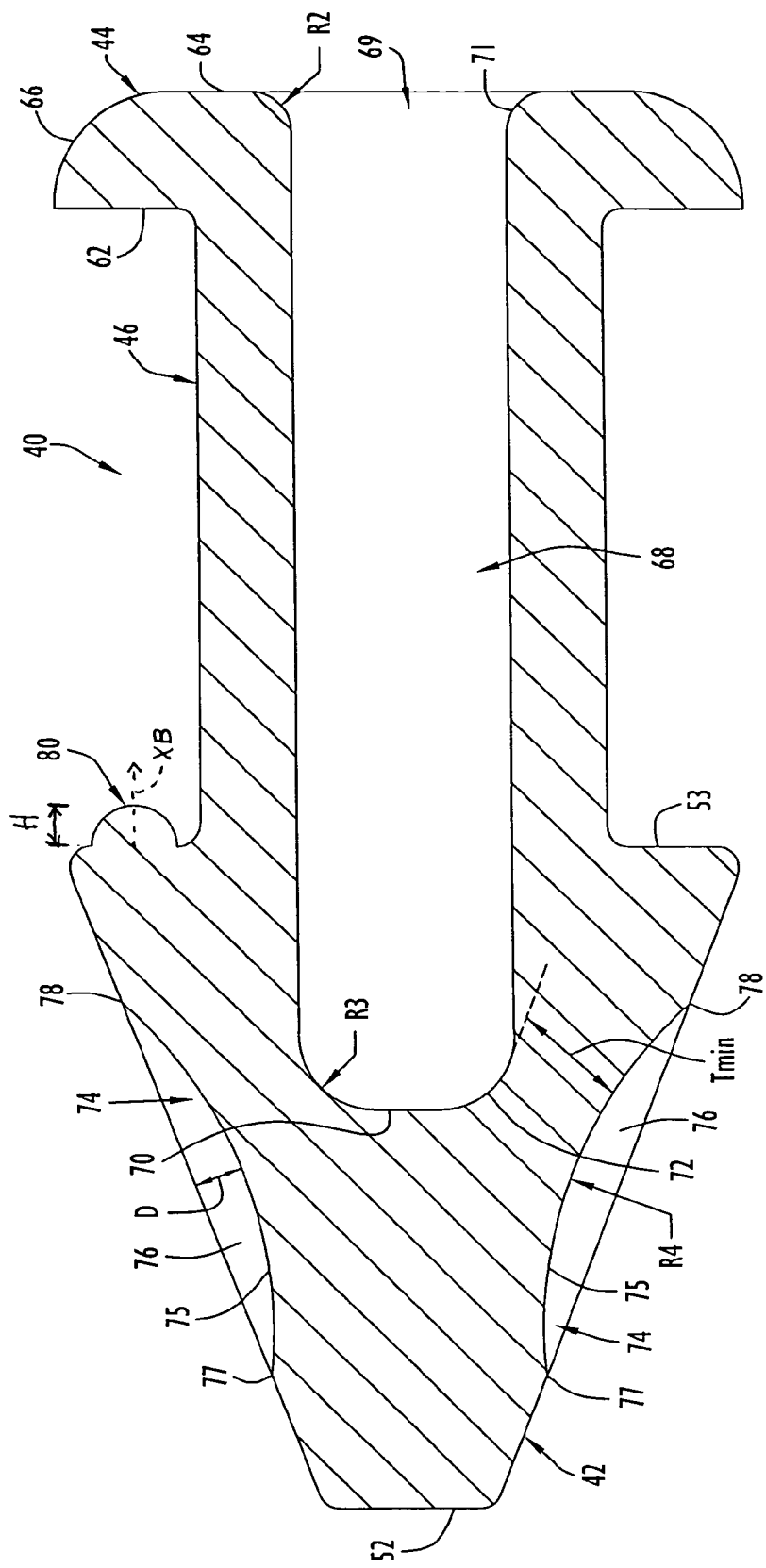
FIG. 6 is a longitudinal sectional view of the punctum plug.

The cap 44 has distal end wall 62 joined to body 46, a proximal or rearward end wall 64, and a side wall 66 joining the distal end wall 62 to the proximal end wall 64. The distal and proximal end walls 62 and 64 have circular peripheral configurations concentric with tip 42 and body 46, the circumference of proximal end wall 64 being smaller than the circumference of distal end wall 62. The distal and proximal end walls 62 and 64 are planar and parallel to one another. The distal and proximal end walls 62 and 64 are also parallel to the forward and rearward end surfaces 52 and 53 of tip 42 and are transverse or perpendicular to the central longitudinal axis X. The side wall 66 of cap 44 curves outwardly in profile with a convex curvature from the periphery or circumference of proximal end wall 64 to the periphery or circumference of distal end wall 62 as best seen in FIGS. 5 and 6. The side wall 66 has a radius of curvature R1 between the periphery or circumference of the proximal end wall 64 and the periphery or circumference of distal end wall 62 providing a smooth, gently rounded transition from the proximal end wall 64 to the distal end wall 62. The cap 44 has a major outer diameter defined by the diameter of the periphery or circumference of distal end wall 62 and has a minor outer diameter defined by the diameter of the periphery or circumference of proximal end wall 64. The major outer diameter of the cap 44 is equal or substantially equal to the maximum external diameter of tip 42. The cap has a height or depth between the distal and proximal end walls 62 and 64. The punctum plug 40 has an overall length between the forward end surface 52 of tip 42 and the proximal end wall 64 of cap 44. The tip 42, cap 44 and body 46 are all concentric with one another and coaxial with the central longitudinal axis X.

The punctum plug 40 has an internal longitudinal passage 68 extending distally therein from an entry opening 69 along the proximal end wall 64 of cap 44 to an internal bottom wall 70 within tip 42 as best seen in FIG. 6. The passage 68 and its entry opening 69 are coaxial with the central longitudinal axis X, and the entry opening 69 has a circular peripheral configuration. The passage 68 is essentially cylindrical in configuration with a uniform or constant diameter between a flared neck 71 circumscribing entry opening 69 and a concave taper 72 adjacent bottom wall 70. As seen in FIG. 6, the neck 71 has a convex curvature with a radius of curvature R2 to provide a smooth, gently curved entry or mouth into the passage 68 for centering and guiding introduction of an insertion tool into the passage. The concave taper 72 joins a side wall of the passage 68 to the bottom wall 70, which is planar and parallel to the proximal end wall 64. The concave taper 72 has a concave curvature with a radius of curvature R3 to provide a smooth, gentle and gradual narrowing transition between the side wall of the passage 68 and the bottom wall 70 to help ensure that the insertion tool is fully inserted and centered in the passage. The passage 68 has a length between the plane containing the proximal end wall 64 and the plane containing the bottom wall 70.

The distal tip 42 has a plurality of insertion guide depressions or slots 74 along the outer surface of the main section 48, and preferably the distal tip 42 has two depressions 74. The depressions 74 extend longitudinally along the main section 48 and have respective central longitudinal axes XD disposed in a plane bisecting the punctum plug 40 along its central longitudinal axis X as best seen from FIG. 7. Accordingly, the central longitudinal axes XD of the depressions 74 are disposed in planes radial to axis X and spaced 180° from one another about the central longitudinal axis X. The central longitudinal axis XD of a first depression 74 may be considered as being located at a first or 0° radial location, and the central longitudinal axis XD of the second depression 74 may be considered as being located at a second or 180° radial location about the central longitudinal axis X.

Figures 3, 4:
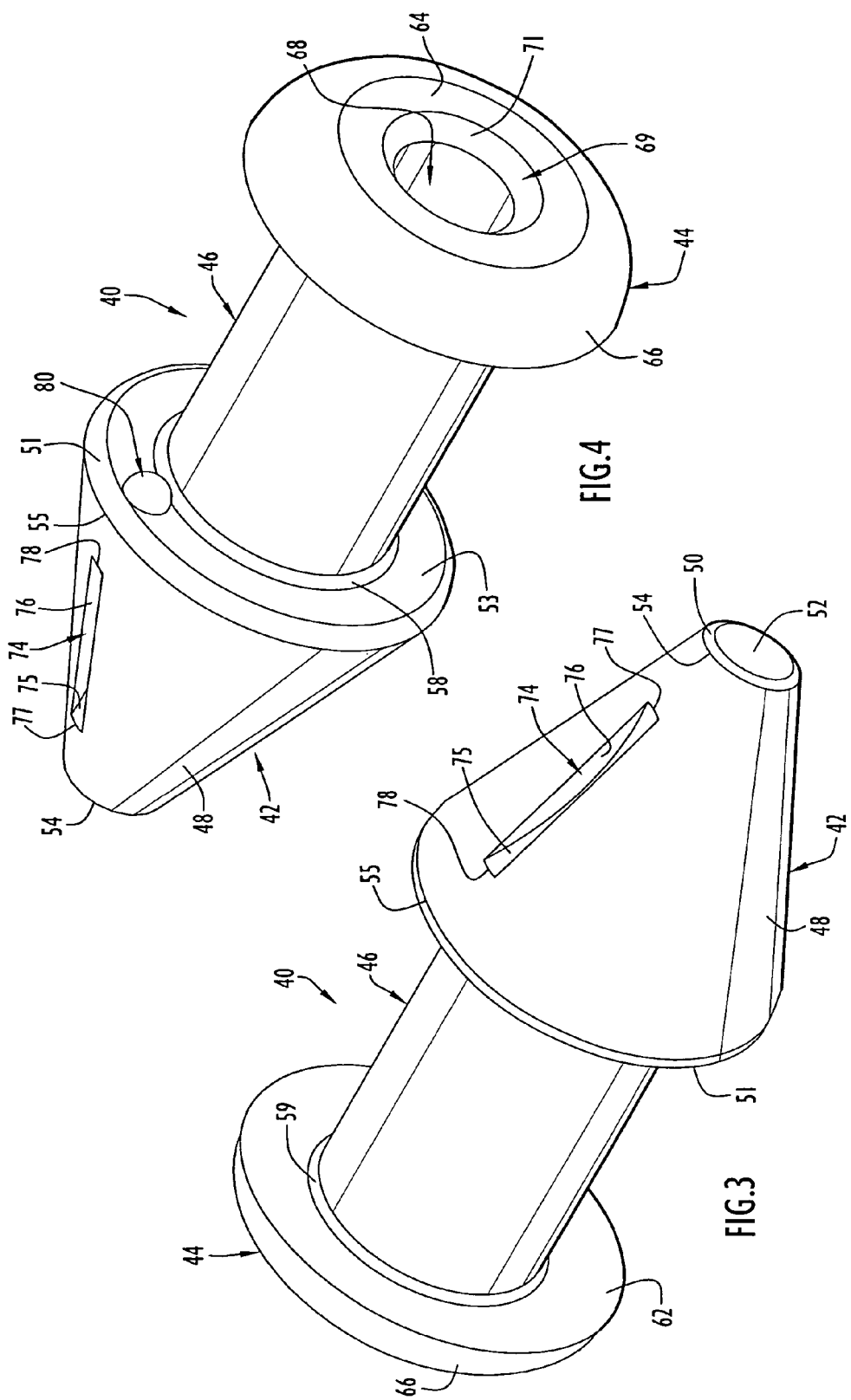
FIG. 3 is a distal perspective view of the punctum plug.
FIG. 4 is a proximal perspective view of the punctum plug.
Figure 7:
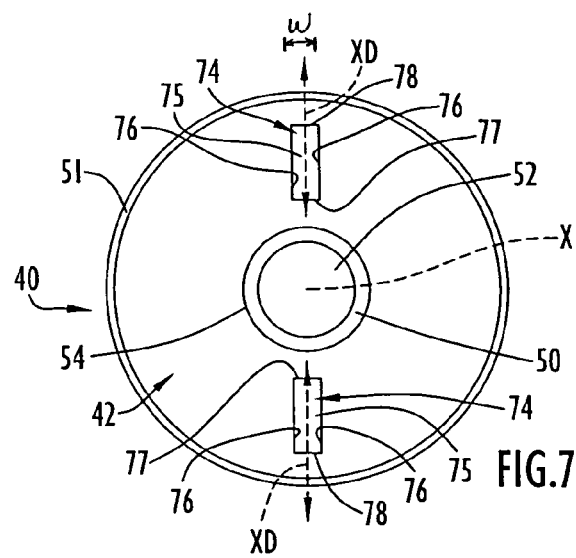
FIG. 7 is a distal end view of the punctum plug.
Figure 8:
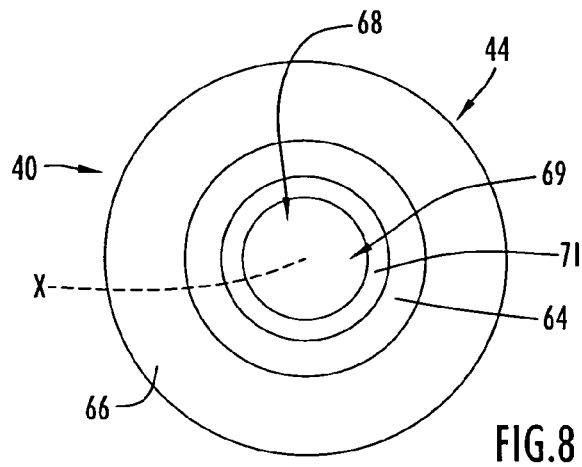
FIG. 8 is a proximal end view of the punctum plug.

Each depression 74 has a continuously curving bottom surface or floor 75 extending beneath the outer surface of the main section 48, and a pair of side walls 76 extending from the floor 75 to the outer surface of the main section 48. The floor 75 of each depression 74 has a continuously curving concave curvature between forward and rearward edges 77 and 78 of the depression at which the floor 75 joins the outer surface of the main section 48 as best shown in FIGS. 3, 6 and 7. The forward and rearward edges 77 and 78 are parallel to each other as well as being perpendicular to the central longitudinal axis XD of the depression. The floor 75 of each depression 74 has a radius of curvature R4, and each depression 74 has a maximum depth D between the floor 75 and the outer surface of the main section 48 as illustrated in FIG. 6. Each depression 74 has a width W between its parallel side walls 76, which are perpendicular to the forward and rearward edges 77 and 78 as seen in FIG. 7. Also, the distal tip 42 has a minimum wall thickness Tmin in a perpendicular direction from a line tangent to concave taper 72, where the concave taper 72 joins the side wall of the passage 68, to the floor 75 as depicted in FIG. 6. Preferably, the maximum depth D for the floor of the depressions is equal or substantially equal to the width W of the depressions.

Figure 9:
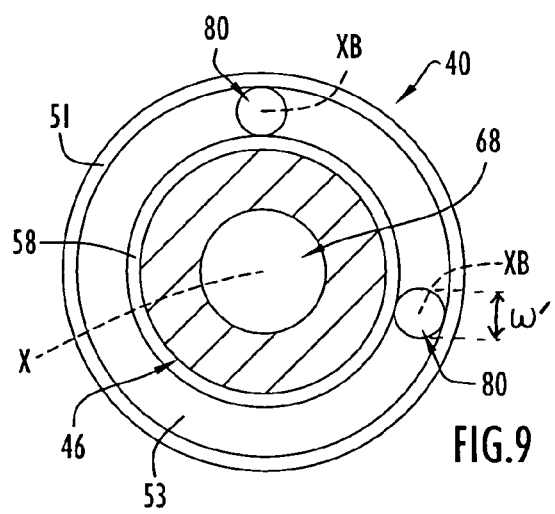
FIG. 9 is a sectional view through a body of the punctum plug taken along line 9-9 of FIG. 5, looking distally.

The distal tip 42 has one or more strengthening beams or protrusions 80 on its rearward end surface 53 and the beams may be referred to as "microbeams" due to their small size. The distal tip 42 is seen as having two strengthening beams 80 on rearward end surface 53. Each beam 80 has a dome-shaped configuration forming a convex protrusion along the rearward end surface 53. Each beam 80 has a base at which the beam is joined to the rearward end surface 53, and the base of each beam is circular on the rearward end surface 53. Each beam 80 has a central axis XB perpendicular to the rearward end surface 53 and parallel to the central longitudinal axis X as depicted in FIGS. 5 and 9, and an apex along the central axis XB. Each beam 80 has a maximum height H along its central axis XB between its apex and the plane containing rearward end surface 53 as shown in FIG. 6. The maximum width W' of each beam 80 is defined by the diameter of its base on the rearward end surface 53 as seen in FIG. 9. Also, the base of each beam 80 has a radius from its central axis XB to its circumference. Preferably, the maximum width W' is about two times the maximum height H such that the maximum height H and the radius at the base are equal or about equal. The beams 80 may be of partial spherical configuration including hemispherical.

In the case of distal tip 42 having two beams 80, the central axes XB of the beams are disposed on the rearward end surface 53 at radial locations spaced 105° or about 105° from one another about the central longitudinal axis X. A first beam 80 has its central axis XB disposed at a first or 0° radial location, and a second beam 80 has its central axis XB disposed at a second radial location spaced 105° or about 105° in a clockwise direction, looking distally, from the first radial location about the central longitudinal axis X as best seen in FIG. 9. Also, it is seen from FIG. 9 that the beams 80 fit between the rearward rim 51 and the forward junction 58.

The punctum plug 40 may be made in its entirety of a biocompatible, medically acceptable elastomeric material including rubber such as silicone rubber. The punctum plug 40 can be fabricated integrally, unitarily or monolithically as one piece. Various manufacturing equipment and processes may be used to fabricate the punctum plug including various micro-molding equipment and processes such as individual compression silicone molding, liquid silicone injection molding and multi-cavity compression molding. The punctum plug 40 will typically be supplied to medical service providers in a medically sterile condition ready for implantation.

The punctum plug 40 is implanted in the lacrimal drainage system 12 by being inserted, distal tip 42 first, into a punctal opening such as lower punctal opening 24b shown in FIGS. 1 and 2. As shown in FIG. 2, a distal end of an insertion tool 84 will normally be removably engaged in the passage 68 with the proximal end of the insertion tool being grasped and manipulated to control the position and movement of the punctum plug during insertion. The punctum plug 40 is advanced distally or forwardly in the punctal opening 24b until the cap 44 is seated on or over the punctal opening 24b and the tip 42 is disposed in the canalicular canal 26b communicating with the punctal opening as depicted in FIG. 2. The tapered configuration of the tip 42 promotes advancement of the punctum plug 40, and the tip 42 assists in centering and aligning the punctum plug in the canalicular canal during insertion. Once the proper position for the punctum plug 40 is obtained, the insertion tool 84 is disengaged therefrom by removing the insertion tool from the passage 69, leaving the implanted punctum plug in place in the lacrimal drainage system 12.

During insertion of the punctum plug 40 into the punctum, the guide depressions 74 enable the punctum plug to better adapt to the particular anatomical characteristics of the punctum and particularly the punctal opening, especially where the punctal opening is non-circular or slit-like. The guide depressions 74 relieve stress on the anatomical tissue of the punctum as the distal tip 42 is inserted and, in particular, when the narrower or shorter dimension of a non-circular punctal opening is widened to allow passage of the distal tip 42 therethrough. The guide depressions 74 present voids which allow the anatomical tissue to non-traumatically "give" and ease insertion of the punctum plug 40. The configuration of depressions 74 ensures that anatomical tissue in contact with the depressions during insertion is not injured or traumatized. The punctum plug 40 can be inserted with the guide depressions 74 selectively oriented relative to the punctum and its punctal opening to best ease and facilitate insertion in accordance with the individual anatomical characteristics of the patient. An individual punctum plug 40 having the guide depressions 74 is thusly better able to facilitate and ease implantation of the punctum plug in puncta having various different anatomical characteristics and anatomically diverse punctal openings. Accordingly, the punctum plug 40 is better adapted for use in a wider range of patients and a wider range of anatomically different puncta and punctal openings.

The beams 80 strengthen and rigidify the punctum plug 40 to resist deformation or collapse, especially during insertion of the punctum plug. The beams 80 assist in maintaining the planarity of the rearward end surface 53 and thusly resist deformation or collapse of the punctum plug 40. As the punctum plug 40 is advanced distally during insertion, the distal tip 42 resists deforming or collapsing, and the punctum plug 40 resists deforming, collapsing or a "noodling" action. The ability of the punctum plug 40 to better resist deforming, collapsing or "noodling" action during insertion facilitates advancement of the punctum plug, promotes proper centering and alignment of the punctum plug to obtain the correct implanted position for the punctum plug, and reduces the difficulty and time required for the implantation procedure.

The punctum plug 40 is shown implanted in FIG. 2 with the distal end wall 62 of cap 44 in abutment with or seated against the rim of anatomical tissue circumscribing or surrounding the punctal opening 24b. The distal end wall 62 is larger in size than the punctal opening 24b to prevent the cap 44 from passing into the punctal opening. The cap 44 covers the punctal opening 24b in its entirety and blocks or occludes the punctal opening to prevent or deter tear fluid or moisture from passing through the punctal opening from the eye. Engagement or abutment of the cap 44 with the anatomical tissue around the punctal opening 24b limits the distance that punctum plug 40 may be advanced during implantation. The distal tip 42 is of a size to forcefully engage the anatomical wall of the canalicular canal 26b to prevent punctum plug 40 from moving proximally or rearwardly so that the punctum plug is anchored in place in the lacrimal drainage system 12. Although the tip 42 is depicted as being anchored in the vertical canalicular canal portion 32b, it should be appreciated that the tip can extend into and/or be anchored within the horizontal canalicular canal portion 34b.

The anchoring effect provided by the distal tip 42 is enhanced in the punctum plug 40 by the depressions 74 and by the strengthening beams 80. Anatomical tissue may enter the depressions 74 to provide a more secure engagement between the punctum plug 40 and the anatomical wall of the canalicular canal 26b for improved anchoring. The configuration of depressions 74 ensures that anatomical tissue is engaged or contacted non-traumatically, while the implanted punctum plug remains in place in the lacrimal drainage system 12. While the implanted punctum plug 40 remains in place in the lacrimal drainage system 12, the strength and rigidity imparted by beams 80 assist the punctum plug in resisting deformation or collapse so that the punctum plug remains securely anchored in place. By helping to maintain the planarity of the rearward end surface 53 of distal tip 42, the beams 80 assist in maintaining the distal tip 42 in secure engagement with the anatomical wall of the canalicular canal 26b. Accordingly, the depressions 74 and/or the beams 80 enhance the anchoring effectiveness of the punctum plug 40 and retard migration of the punctum plug 40 from its implanted position.

The anchoring force or pressure provided by tip 42 on the wall of canalicular canal 26b is overcome when the punctum plug 40 is forcefully withdrawn from the canalicular canal and the punctal opening 24b for removal from the eye. The configuration of depressions 74 and the dome-like configuration of beams 80 ensure that anatomical tissue is not damaged or traumatized during withdrawal and ensure that withdrawal is not made more difficult due to the presence of the depressions 74 and the beams 80.

In an illustrative, but not limiting, embodiment of punctum plug 40, the punctum plug has an overall length of about 0.06 inch; the distal tip has a length of about 0.028 inch, a maximum external diameter of about 0.029 inch, and a minimum external diameter of about 0.007 inch; the rearward rim of the tip has a radius of curvature of about 0.001 inch; the insertion guide depressions have a width of about 0.002 inch and a maximum depth of about 0.002 inch; the floor of the depressions has a radius of curvature R4 of about 0.0192 inch; the tip has a minimum wall thickness Tmin of about 0.002 inch; the beams are hemispherical or substantially hemispherical in configuration with a maximum height H of about 0.0018 inch and a radius at the base of about 0.0018 inch; the body including the forward and rearward junctions has a length of about 0.027 inch and an outer diameter between the forward and rearward junctions of about 0.017 inch; the cap has a height of about 0.005 inch and a major diameter of about 0.029 inch; the side wall of the cap has a radius of curvature R1 of about 0.005 inch; the passage has a length of about 0.043 inch and a diameter of about 0.009 inch; the neck has a radius of curvature R2 of about 0.002 inch; and the concave taper has a radius of curvature R3 of about 0.003 inch. The illustrative dimensions for punctum plug 40 may be considered illustrative of a "small" size punctum plug. As described further below, the punctum plug may be made available in different sizes corresponding to different anatomical sizes of punctal openings and canalicular canals.

Figure 10:
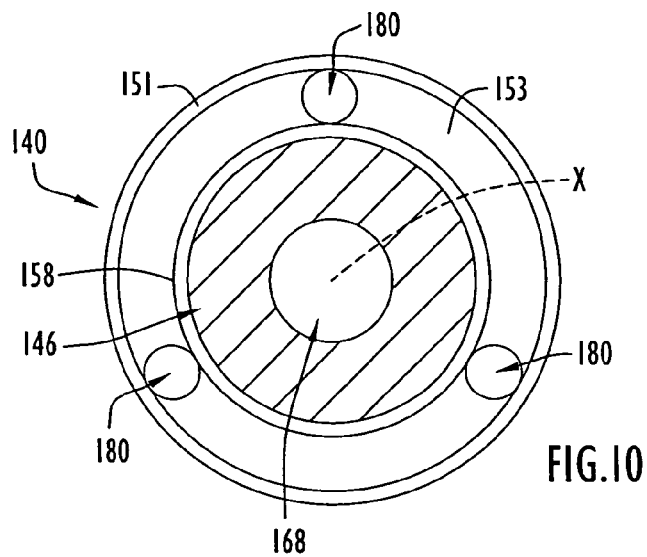
FIG. 10 is a sectional view through the body of an alternative punctum plug of the present invention, looking distally.

A modified punctum plug is depicted at 140 in FIG. 10 in sectional view like that depicted in FIG. 9 for punctum plug 40. The punctum plug 140 is similar to punctum plug 40 but has three strengthening beams 180 on the rearward end surface 153 of its distal tip 142. The strengthening beams 180 are disposed at radial locations equally spaced about the central longitudinal axis X of the punctum plug 140 so that the central axes of the strengthening beams 180 are disposed at radial locations spaced 120° from one another about the central longitudinal axis X. Accordingly, a first strengthening beam 180 is disposed at a first or 0° radial location, a second strengthening beam 180 is disposed at a second or 120° radial location, and a third strengthening beam 180 is disposed at a third or 240° radial location about the central longitudinal axis X.

The punctum plug 140 may be of a different size than punctum plug 40. In an illustrative but not limiting embodiment of punctum plug 140, the punctum plug 140 may be a "medium" size punctum plug in which the punctum plug has an overall length of about 0.063 inch; the tip 142 has a length of about 0.031 inch, a maximum external diameter of about 0.033 inch, and a minimum external diameter of about 0.008 inch; the two insertion guide depressions (not seen in FIG. 10) for punctum plug 140 are like the insertion guide depressions 74 for punctum plug 40; the tip 142 has a minimum wall thickness Tmin (not seen in FIG. 10) like that for distal tip 42; the strengthening beams 180 are hemispherical or substantially hemispherical in configuration with a maximum height of about 0.002 inch and a radius at the base of about 0.002 inch; the body 146 including the forward junction 158 and the rearward junction (not seen in FIG. 10) has a length of about 0.027 inch like the body of punctum plug 40; the body 146 has an outer diameter of about 0.02 inch; the cap (not seen in FIG. 10) has a height of about 0.005 inch and a major diameter of about 0.033 inch; the side wall of the cap has a radius of curvature of about 0.005 inch like the radius of curvature R1 of punctum plug 40; the passage 168 has a length of about 0.043 inch and a diameter of about 0.009 inch like punctum plug 40; and the radii of curvature of the neck and the concave taper (not shown in FIG. 10) are like those (R2, R3) of punctum plug 40.

Figure 11:
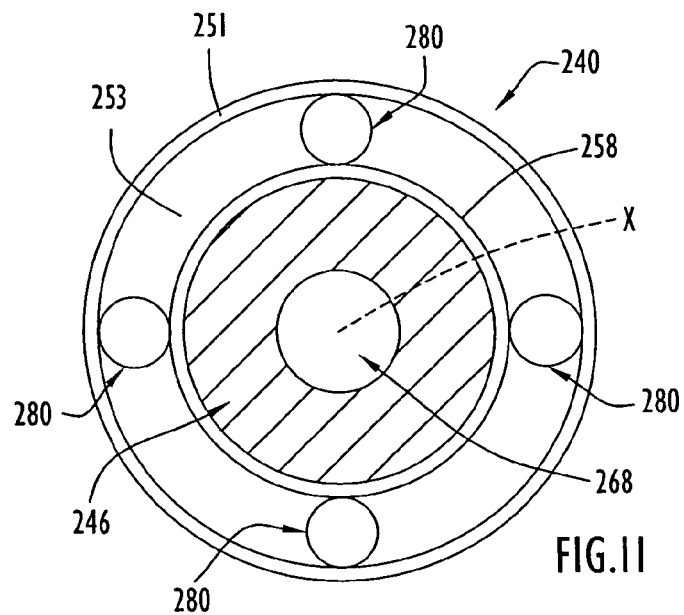
FIG. 11 is a sectional view through the body of another alternative punctum plug of the present invention, looking distally.

Another modified punctum plug is depicted at 240 in FIG. 11 in sectional view like that depicted for punctum plugs 40 and 140. The punctum plug 240 is similar to punctum plugs 40 and 140 but has four strengthening beams 280 on the rearward end surface 253 of its distal tip 242. The strengthening beams 280 are disposed on the rearward end surface 253 at equally spaced radial locations about the central longitudinal axis X of the punctum plug 240. The central axes of the strengthening beams 280 are thusly located at radial locations spaced 90° from one another about the central longitudinal axis X. A first strengthening beam 280 is located at a first or 0° radial location, a second strengthening beam 280 is located at a second or 90° radial location, a third strengthening beam 280 is located at a third or 180° radial location, and a fourth strengthening beam 280 is located at a fourth or 270° radial location about the central longitudinal axis X.

The punctum plug 240 may be of a different size than the punctum plugs 40 and 140. In an illustrative but not limiting embodiment of punctum plug 240, the punctum plug 240 may be a "large" size punctum plug in which the punctum plug has an overall length of about 0.07 inch; the distal tip 242 has a length of about 0.038 inch, a maximum external diameter of about 0.037 inch, and a minimum external diameter of about 0.007 inch; the two insertion guide depressions (not seen in FIG. 11) for punctum plug 240 are like those for punctum plugs 40 and 140; the tip 242 has a minimum wall thickness Tmin (not seen in FIG. 11) like that for punctum plugs 40 and 140; the beams 280 are partial spherical in configuration with a maximum height of about 0.002 inch and a radius at the base of about 0.0026 inch; the length of the body 146 and the height of the cap (not seen in FIG. 11) are like that for punctum plugs 40 and 140; the body 146 has an outer diameter of about 0.022 inch; the side wall of the cap has a radius of curvature of about 0.005 inch like the radius of curvature R1 of punctum plug 40; the cap has a major diameter of about 0.037 inch; the length and the diameter of the passage 268 are like those for punctum plugs 40 and 140; and the radii of curvature for the neck and the concave taper (not shown in FIG. 11) for passage 268 are like those (R2,R3) for punctum plugs 40 and 140.

Figure 12:
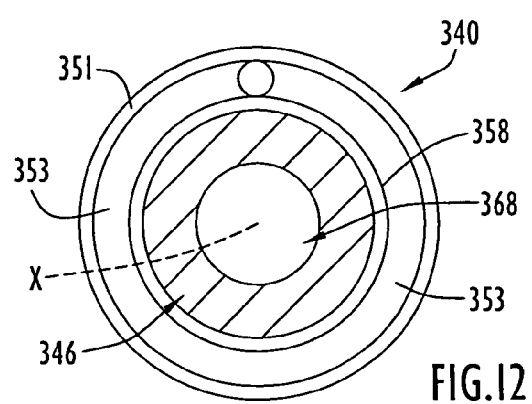
FIG. 12 is a sectional view through the body of a further alternative punctum plug of the present invention, looking distally.

An additional modified punctum plug is depicted at 340 in FIG. 12. The punctum plug 340 is similar to punctum plugs 40, 140 and 240 but has a single strengthening beam 380 on the rearward end surface 353 of its distal tip 342. The strengthening beam 380 is located on the rearward end surface 353 with its center axis at a 0° radial location with respect to the central longitudinal axis X of the punctum plug 340.

The punctum plug 340 may be of a different size than the punctum plugs 40, 140 and 240. In an illustrative but not limiting embodiment of punctum plug 340, the punctum plug 340 may be an "extra small" size punctum plug in which the punctum plug has an overall length of about 0.056 inch; the distal tip 342 has a length of about 0.024 inch, a maximum external diameter of about 0.026 inch, and a minimum external diameter of about 0.008 inch; the punctum plug 340 has two insertion guide depressions (not seen in FIG. 12) that are like the insertion guide depressions of punctum plugs 40, 140 and 240; the distal tip 342 has a minimum wall thickness (not seen in FIG. 12) like the minimum wall thickness Tmin for punctum plugs 40, 140 and 240; the strengthening beam 380 is hemispherical or substantially hemispherical in configuration with a maximum height of about 0.0013 inch and a radius at the base of about 0.0013 inch; the body 346 has an outer diameter of about 0.016 inch and a length like that for punctum plugs 40, 140 and 240; the cap (not seen in FIG. 12) has a major diameter of about 0.026 inch; the height of the cap is like that for punctum plugs 40, 140 and 240; the side wall of the cap has a radius of curvature of about 0.004 inch; the passage 368 has a length of about 0.04 inch and a diameter like that for the passages of punctum plugs 40, 140 and 240; and the radii of curvature for the neck and the concave taper (not shown in FIG. 12) are like those (R2, R3) for punctum plugs 40, 140 and 240.

In the punctum plugs 40, 140, 240 and 340, the number of strengthening beams on the rearward end surface of the punctum plugs can be used to indicate the size of the punctum plugs. In particular, one strengthening beam identifies the punctum plug as an "extra small" size punctum plug; two strengthening beams identifies the punctum plug as a "small" size punctum plug; three strengthening beams identifies the punctum plug as a "medium" size punctum plug; and four strengthening beams identifies the punctum plug as a "large" size punctum plug. The size of a punctum plug can thusly be identified or ascertained visually merely by viewing the punctum plug and noting the number of strengthening beams, as typically assisted with microscopic magnification. Because the strengthening beams are protrusions, they stand out more prominently and are more visible such that size identification can be accomplished more quickly and with greater certainty. The size of a punctum plug can be determined visually in this manner prior to implantation to ensure that the correct size punctum plug is selected for implantation to obtain the proper fit in the lacrimal drainage system of the patient.

Although it is preferred to provide the punctum plugs with both insertion guide depressions and one or more strengthening beams, it should be appreciated that punctum plugs can be provided having either insertion guide depressions or one or more strengthening beams since each imparts its own benefits and advantages.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A punctum plug for implantation in the lacrimal drainage system of the eye, comprising an anchor member having a forward end surface, a rearward end surface and a main section extending longitudinally between said forward end surface and said rearward end surface, said main section having an outer surface;

a proximal cap having a forward end wall;

a body connecting said rearward end surface to said forward end wall and having a central longitudinal axis coaxial with a central longitudinal axis of said punctum plug;

a plurality of depressions in said anchor member extending longitudinally along said outer surface, said depressions presenting voids open along said outer surface during insertion of said punctum plug in the lacrimal drainage system; and one or more strengthening protrusions on said rearward end surface, each of said protrusions being centered on a center axis of said protrusion that is located on said rearward end surface at a radially offset location from said central longitudinal axis of said body, said anchor member being insertable through the punctal opening of the lacrimal drainage system and into the canalicular canal communicating with the punctal opening with said cap remaining exposed in the eye in an implanted position for said punctum plug in the lacrimal drainage system.

2. The punctum plug recited in claim 1 wherein said main section has a frustoconical configuration tapering toward said forward end surface and said plurality of depressions comprises a pair of said depressions having respective central longitudinal axes in a plane bisecting said anchor member along said central longitudinal axis of said punctum plug.

3. The punctum plug recited in claim 2 wherein each of said depressions has a concave floor extending between forward and rearward edges of said depressions on said outer surface of said main section, and side walls extending from said floor to said outer surface.

4. The punctum plug recited in claim 3 wherein said forward and rearward edges of each of said depressions are parallel and are perpendicular to said central longitudinal axis of said depression.

5. The punctum plug recited in claim 1 wherein each of said protrusions has a partial spherical configuration.

6. The punctum plug recited in claim 5 wherein each of said protrusions has a hemispherical configuration.

7. The punctum plug recited in claim 1 wherein each of said protrusions has a maximum width at a base of said protrusion along said rearward end surface and a maximum height extending from said base in the direction of said cap, said maximum width being about two times said maximum height.

8. The punctum plug recited in claim 1 wherein said one or more strengthening protrusions includes one of said protrusions on said rearward end surface.

9. The punctum plug recited in claim 1 wherein said one or more strengthening protrusions includes two of said protrusions on said rearward end surface and said center axes of said protrusions are located on said rearward end surface at respective radially offset locations spaced about 105° from each other about said central longitudinal axis of said body.

10. The punctum plug recited in claim 1 wherein said one or more strengthening protrusions includes three of said protrusions on said rearward end surface and said center axes of said protrusions are located on said rearward end surface at respective radially offset locations equally spaced about said central longitudinal axis of said body.

11. The punctum plug recited in claim 1 wherein said one or more strengthening protrusions includes four of said protrusions on said rearward end surface and said center axes of said protrusions are located on said rearward end surface at respective radially offset locations equally spaced about said central longitudinal axis of said punctum plug.

12. The punctum plug recited in claim 1 wherein the number of said protrusions on said rearward end surface is indicative of the size of said punctum plug.

13. The punctum plug recited in claim 1 and further comprising an internal longitudinal passage within said punctum plug.

14. The punctum plug recited in claim 13 wherein said proximal cap has a rearward end wall, said longitudinal passage has an opening along said rearward end wall, and said longitudinal passage extends longitudinally from said opening along said rearward end wall toward said forward end surface of said anchor member.

15. The punctum plug recited in claim 14 wherein said longitudinal passage extends longitudinally from said opening to terminate at an internal wall within said punctum plug.

16. A punctum plug for implantation in the lacrimal drainage system of the eye, comprising a distal tip having a forward end surface at a forward end of said distal tip, a rearward end surface at a rearward end of said distal tip and a main section between said forward end surface and said rearward end surface, said forward and rearward end surfaces being transverse to a central longitudinal axis of said punctum plug, said main section having an outer surface with a maximum external dimension at said rearward end and a minimum external dimension at said forward end;

a proximal cap having a forward end wall transverse to said central longitudinal axis of said punctum plug;

a body connecting said rearward end surface to said forward end wall;

a plurality of longitudinal slots in said distal tip presenting voids open along said outer surface during insertion of said punctum plug in the lacrimal drainage system of the eye, said slots having respective central longitudinal axes in planes radial to said central longitudinal axis of said punctum plug; and one or more convex strengthening protrusions on said rearward end surface, each of said protrusions being centered on a center axis located on said rearward end surface between said body and said maximum external dimension of said main section of said distal tip, said distal tip being insertable through the punctal opening of the lacrimal drainage system and into the canalicular canal communicating with the punctal opening with said cap remaining exposed in the eye in an implanted position for said punctum plug in the lacrimal drainage system.

17. The punctum plug recited in claim 16 wherein said rearward end surface and said forward end wall are perpendicular to said central longitudinal axis of said punctum plug.

18. The punctum plug recited in claim 16 wherein said plurality of longitudinal slots comprises two of said slots having said respective central longitudinal axes in said planes spaced 180° from one another about said central longitudinal axis of said punctum plug.

19. The punctum plug recited in claim 16 wherein each of said slots comprises a continuously curving concave floor extending between forward and rearward edges of said slots on said outer surface of said main section, and a pair of parallel side walls extending from said floor to said outer surface, each of said sots having a maximum depth of about 0.002 inch and a width between said side walls of about 0.002 inch.

20. The punctum plug recited in claim 16 wherein each of said protrusions includes a circular base joined to said rearward end surface and having a radius, each of said protrusions has an apex along said center axis and a height between said apex and said rearward end surface, said radius being in the range of about 0.0013 inch to about 0.0026 inch, and said height being equal or substantially equal to said radius.

21. The punctum plug recited in claim 16 wherein said proximal cap has a rearward end wall, said punctum plug includes an internal longitudinal passage having an opening along said rearward end wall, and said longitudinal passage extends longitudinally from said opening toward said forward end surface of said distal tip.

22. The punctum plug recited in claim 21 wherein said internal longitudinal passage extends from said opening to terminate at an internal bottom wall within said distal tip, said bottom wall being joined to a side wall of said passage by a concave taper, said distal tip having a minimum wall thickness of about 0.002 inch between said concave taper and said floor of each of said depressions.

23. The punctum plug recited in claim 21 wherein said punctum plug has a length between said forward end surface and said rearward end wall, and said longitudinal passage extends longitudinally within said punctum plug less than the entirety of said length.

24. A punctum plug for implantation in the lacrimal drainage system of the eye, comprising a distal tip having an outer surface of frustoconical configuration tapering in a forward direction between a planar rearward end surface of said distal tip and a forward end surface of said distal tip, said distal tip being coaxial with a central longitudinal axis of said punctum plug and said rearward end surface being perpendicular to said central longitudinal axis of said punctum plug;

a proximal cap having a planar forward end wall parallel to said rearward end surface;

a cylindrical body connecting said rearward end surface to said forward end wall, said body being coaxial with said central longitudinal axis;

an internal passage in said punctum plug coaxial with said central longitudinal axis and extending from an entry opening on said cap toward said forward end surface of said distal tip;

a pair of slots in said distal tip extending longitudinally along said outer surface at 180° spaced radial locations about said central longitudinal axis of said punctum plug to facilitate insertion of said punctum plug in the lacrimal drainage system of the eye, each of said slots having a concavely curved floor that meets said outer surface at opposite ends of said floor and a pair of side walls extending from opposed sides of said floor to said outer surface, each of said slots having a width between said side walls and a maximum depth between said floor and said outer surface about equal to said width; and one or more convex strengthening beams protruding from said rearward end surface, each of said beams being centered on a center axis located on said rearward end surface parallel to said central longitudinal axis of said punctum plug, a maximum width at a base of said beam along said rearward end surface and a maximum height along said center axis of said beam, said maximum height being about one half said maximum width, said distal tip being insertable through the punctal opening of the lacrimal drainage system and into the canalicular canal communicating with the punctal opening with said cap remaining exposed in the eye in an implanted position for said punctum plug in the lacrimal drainage system 25. The punctum plug recited in claim 24 wherein the number of said beams is indicative of the size of said punctum plug.

26. The punctum plug recited in claim 24 wherein said forward end surface comprises a forward wall defining a closed forward end for said distal tip.

* * * * *